United States Patent
Blacker et al.

(12) 
(10) Patent No.: US 6,258,967 B1
(45) Date of Patent: Jul. 10, 2001

(54) PROCESS FOR THE PREPARATION OF AN ORGANOZINC REAGENT

(75) Inventors: Andrew John Blacker; Jan Michael Fielden, both of Huddersfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/331,451

(22) PCT Filed: Dec. 15, 1997

(86) PCT No.: PCT/GB97/03443

§ 371 Date: Jun. 21, 1999

§ 102(e) Date: Jun. 21, 1999

(87) PCT Pub. No.: WO98/28306

PCT Pub. Date: Jul. 2, 1998

(30) Foreign Application Priority Data

Dec. 21, 1996 (GB) .................................... 9626635

(51) Int. Cl.[7] .................. C07F 3/06; C07C 45/00
(52) U.S. Cl. .............. 556/121; 549/3; 549/206; 546/2; 546/10; 568/317
(58) Field of Search ................ 556/121; 549/3, 549/206; 546/2, 10; 568/317

(56) References Cited

FOREIGN PATENT DOCUMENTS 2 663 032    12/1991   (FR) .

OTHER PUBLICATIONS

Brooker et al., Organometallics, vol. 11, No. 1, pp. 192–195.*
Luche et al: "Ultrasound in organic sysnthesis.4.a simplified preparation of diarylzinc reagents and their conjugate addition to alpha–enones", THE JOURNAL OF ORGANIC CHEMISTRY, vol. 48, 1983, pp. 3837–3839, XP002056563.
Petrier et al: "Ultrasound in organic synthesis.7.preparation of organozinc reagents and their nickel–catalyzed reactions with alpha,beta–unsaturated carbonyl compounds", THE JOURNAL OF ORGANIC CHEMISTRY, vol. 50, 1985, pp. 5761–5765, XP002056564.

* cited by examiner

*Primary Examiner*—Porfirio Nazario-Gonzalez
(74) *Attorney, Agent, or Firm*—Pillsbury Winthrop LLP

(57) ABSTRACT

A process for the preparation of an aromatic organozinc compound is provided. The process comprises reacting a zinc chloride, bromide or iodide and an organometallic compound of another metal comprising an aromatic moiety, producing a reaction product comprising an organozinc compound and a halide salt of the other metal. The reaction product is then contacted with a liquid hydrocarbon, in which the organozinc compound is soluble and the halide salt of the other metal is of low solubility. The halide salt of the other metal is separated from the hydrocarbon, and the organozinc compound can be recovered from the hydrocarbon. Organozinc compounds produced by this process can be employed to generate chiral centres in suitable substrates.

29 Claims, No Drawings

PROCESS FOR THE PREPARATION OF AN ORGANOZINC REAGENT

This application is a national phase of international application PCT/GB97/03443 filed Dec. 15, 1997 which designated the U.S.

This invention relates to a process for the preparation of an organozinc reagent, more specifically to the preparation of organozinc reagents comprising an aromatic moiety, to compositions comprising organozinc reagents, and to processes for the use of such reagents and compositions.

Organozinc reagents may be made by reacting a zinc halide with an organic compound of another metal. The co-product of such a reaction is a halide of that other metal. To purify the organozinc compound, it has been proposed in the case of aromatic organozinc compounds, and when the other metal is magnesium, to precipitate its halide by adding 1,4-dioxan, (e.g. Nutzel in Houben-Weyls Methoden der organischen Chemie 1973, XIII/2a, 197–198, 592–599 and Soai et al. J. Chem. Soc. Perkin Trans. 1991. 1613–1615, based on Schlenk et al. Ber. 1929, LXII, 920–924). However, the organozinc compounds so produced have been found to be unsuitable for use in asymmetric synthesis.

We have now devised a simpler process for purifying aromatic organozinc compounds. Our process is applicable to a wider range of 'other' metals and to purifying aromatic organozinc reagents in which the organic groups are such that distillation would not be convenient. The organozinc reagents so produced are believed to be in a state different in point of purity from that resulting from the dioxan process, and in at least some aspects, are believed to be more suitable for enantioselective synthesis.

According to a first aspect of the present invention, there is provided a process for the preparation of an organozinc compound comprising an aromatic moiety by reaction between a zinc chloride, bromide or iodide and an organometallic compound of another metal comprising an aromatic moiety, thereby producing a reaction product comprising an organozinc compound and a halide salt of the other metal, the reaction product being contacted with a liquid in which the organozinc compound is soluble and the halide salt of the other metal is of low solubility, and separating the halide salt of the other metal from the liquid, characterised in that the liquid is a hydrocarbon.

The organozinc compound can be recovered from the liquid, or can be employed as a reagent as a solution in the liquid.

The hydrocarbon in which the organozinc compound is soluble and the co-product halide is of low solubility can be linear, branched or cyclic. Aliphatic and particularly aromatic hydrocarbons are most commonly employed. Examples of suitable aliphatic hydrocarbons include petroleum ethers; linear or branched alkanes, particularly those having from 5 to 22 carbon atoms, and preferably from 6 to 14 carbon atoms; kerosenes; and cyclic hydrocarbons, particularly those comprising a 5 to 8 membered alicyclic ring. Many suitable hydrocarbons have a boiling point at atmospheric pressure in the range of from 60 to 130° C. Examples of suitable aromatic hydrocarbons include those comprising from 6 to 10 carbon atoms, and include benzene and alkyl-substituted benzenes. Preferred hydrocarbons include hexane and cyclohexane, and particularly preferred hydrocarbons are toluene, xylene and mesitylene. The hydrocarbon need not itself be a liquid at ambient temperature, provided it forms a liquid system at processing temperatures in presence of other materials present, and so for example, butane may be employed under suitable pressure conditions.

The liquid may be a mixture of one or more hydrocarbons. The liquid may also comprise one or more other compounds, providing that the solubility of the undesired metal halide in the liquid is not increased to an unacceptable level thereby.

If desired, the contact between the reaction product and the hydrocarbon may be preceded by a conventional dioxan addition and removal of the resulting metal halide precipitate as a first crude purification step, with the resultant dioxan-zinc solution being contacted with the hydrocarbon as a polishing step to precipitate further metal halide.

At least one of the organic groups in the organozinc compound prepared by the process of the present invention comprises an aromatic moiety. Examples of suitable aromatic moieties include particularly phenyl and naphthyl groups. The aromatic moiety may be a heteroaromatic group, especially a furyl, pyridyl, quinolyl or thienyl group; a metalloaromatic group such as ferrocenyl; or an araliphatic group, particularly a benzyl group. The second of the organic groups in the organozinc compound can be a second aromatic group, or may be a non-aromatic group. Where a non-aromatic group is present, the group can be an aliphatic group especially a $C_{1-20}$, particularly a $C_{1-12}$, aliphatic, and preferably alkyl, group and most preferably a methyl, trihalomethyl, such as trifluoromethyl, ethyl, pentahaloethyl, such as pentafluoroethyl, n- or iso-propyl, or n-, iso- or tert-butyl group; a cycloaliphatic, especially a $C_{3-8}$ cycloaliphatic group, preferably a cyclopropyl, cyclobutyl, cyclopentyl or cyclohexyl group, a carbonlinked heterocyclic group, or a hydrogenated derivative of an aromatic group. The non-aromatic groups may be saturated or unsaturated. The organic groups in the organozinc compound may carry one or more substituents. There may be present organic groups of more than one type, as the result for example of using a mixture of starting materials or mixing single-type reagents without or with disproportionation.

Organometallic compounds which can be reacted with zinc halides in the process according to the present invention include organic compounds of alkaline metals and alkaline earth metals, particularly organomagnesium compounds and organolithium compounds, organoaluminium, organoborane, organotin, organocuprate, organocerium organocadmium and organomercury compounds. The nature of the organic group(s) in the organometallic compound will be selected so as to introduce the desired organic groups into the organozinc compound. Accordingly, an organometallic compound comprising at least one aromatic moiety must be employed. Correspondingly, where an organozinc compound comprising a non-aromatic group is to be produced, an organometallic compound comprising such a group can also be employed. Example of suitable organomagnesium compounds include organomagnesium halides, particularly optionally substituted alkyl and aryl magnesium halide compounds, and particularly optionally substituted $C_{1-6}$ alkyl or optionally substituted phenyl magnesium halides. Examples of suitable organolithium compounds include optionally substituted alkyl and aryl lithium compounds, and particularly optionally substituted Con alkyl or optionally substituted phenyl lithium compounds. Further suitable organolithium compounds are organolithium halides, such as optionally substituted alkyl and aryl lithium halide compounds, especially optionally substituted $C_{1-4}$ alkyl or optionally substituted phenyl lithium halide compounds, and particularly organolithium chlorides and bromides. Preferred organolithium compounds include methyllithium, trifluoromethyllithium, ethyllithium, n- and iso-propyllithium, and n-, iso and tert-butyllithium, phenyllithium and the chlorides and bromides of methyllithium, trifluoromethyllithium, ethyllithium, n- and isopropyllithium, and n-, iso- and tert-butyllithium and phenyllithium.

When the said 'other' metal is magnesium, the organometallic compound is conveniently a Grignard reagent, that is, introduced as an ethereal solution of a compound of stoichiometry R—Mg—X, where R is the required organic group and X is chlorine, bromine or iodine. The solvent is commonly an ether, such as a di($C_{1-6}$ alkyl) ether, for example diethyl ether, dibutyl ether, diisoamyl ether and glyme. Asymmetric dialkyl ethers can also be employed, such as t-butylmethylether. Other ethers that may be employed include diglyme and tetrahydrofuran, THF being usually preferred because of its capacity to dissolve compounds having a greater range of groups R. The ether quantity may if desired be less than sufficient to dissolve the whole of the Grignard reactant.

In certain embodiments, a mixture of different organometallic compounds can be employed to produce a mixed organozinc compound. Approximately equal amounts of such different organometallic compounds would often be employed in such embodiments.

The mole ratio of organometallic compound to zinc chloride, bromide or iodide is often selected to be in the range of from 1:1 to 3:1, and preferably from 2:1 to 2.5:1. When a mixture of different organometallic compounds is employed, the total amount of such compounds is selected to be within this range.

The zinc chloride, bromide or iodide employed is preferably zinc bromide.

The reaction between the zinc chloride, bromide or iodide and the organometallic compound conveniently takes place in the presence of a solvent. Examples of suitable solvents include ethers, commonly di($C_{1-6}$ alkyl) ethers, including diethyl ether, dibutyl ether, diisoamyl ether and glyme. Asymmetric dialkyl ethers can also be employed, such as t-butylmethylether. Other ethers that may be employed include diglyme and tetrahydrofuran. In certain embodiments of the present invention, especially when an organolithium compound is employed as organometallic compound, the solvent comprises a hydrocarbon, thereby achieving the reaction and contact of the reaction product with a hydrocarbon in a single step. Further contacts with hydrocarbon may additionally be employed.

Advantageously, the organometallic compound is introduced into the reaction mixture in the form of a solution in the solvent in which it has been prepared. This solvent will depend on the exact nature of the organometallic compound, but is conveniently an ether, particularly one or more of the ethers listed above a suitable reaction solvents. Organolithium compounds particularly can be introduced as a solution in a mixture of an ether and a hydrocarbon solvent. When such a mixed solvent is employed, the hydrocarbon conveniently comprises at least 50% by weight of the solvent.

The reaction temperature is typically in the range of from −30 to 150, and especially 10 to 120° C. Conveniently, a temperature of from ambient up to the reflux temperature of any solvent(s) present may be employed. Reaction times are typically in the range 0.5 to 100 hours, especially 1 to 48 hours and preferably from 2 to 15 hours. Times and temperatures should be sufficient to disproportionate any organozinc halide which may be formed during the reaction. Atmospheric pressure is suitable, unless components of unusually low or high volatility are being used.

Before contacting the reaction product with the liquid, any solvent already present, such as ether solvent in which the compound of the said other metal is introduced may be removed, for example by distillation, possibly at subatmospheric pressure. However, advantageously, such solvent is not removed prior to contact with the liquid. Preferably, the liquid employed has a higher boiling point than any other solvent present. Accordingly, after addition of an aliquot of the liquid, the more volatile other solvent can be removed by distillation or by azeotroping. A further aliquot of the liquid can be added if desired. This procedure may be repeated one or more times. Removal of the other solvent followed by addition of a further charge of liquid is most preferably employed when the other metal halide is a magnesium halide. The resulting solution of organozinc reagent may be passed to reaction with a substrate compound as hereinafter defined, or stored as such, or concentrated, possibly with crystallisation if its structure so permits.

If desired, the reaction can be carried out on a one-pot basis from magnesium or other reactive metal, zinc halide and organic halide, possibly aided by ultrasound (Luche et al. J Org Chem 1983 48 (21) 3837–3839).

In the ensuing description, definitions of carbon chain length by reference to the numerical extremities of a range are to be understood as including all the members of the range.

The organozinc reagent product preferably contains less than 20, especially less than 5, especially less than 1, % w/w of other metal, calculated as % of total metal. Such a content of metal halide appears to correspond to a substantial absence of material effective to cause competing achiral catalysis to form a racemic product. Zinc reagent having the so-defined content of metal halide is provided by the process of the first aspect of the invention as a solution or as a solid,-possibly crystalline. If the reagent is in solution, the solvent is preferably one or more of the liquids defined above.

The organozinc reagent may if desired be further purified by contacting with active carbon or a chelating ligand such as a 2,2'-bipyridyl that forms an insoluble complex with metal halide and/or possibly by vacuum distillation. The reagent, whether or not so further purified, may be used as an intermediate for producing a semiconductor, for example by vapour deposition or epitaxy.

It is believed that the organozinc reagent prepared in the process of the present invention can form complexes with chelating compounds catalytic for its reaction with an aldehyde. The chelate compound is derived for example from a chelator selected from aminoalcohol, diamine or diol, in which the chelating groups are separated by 2 or 3 carbon atoms, as in a 1,2- or 1,3-hydroxy- or mercapto-amine. The chelate compound may comprise a Lewis acid, for example lithium, boron, titanium or zinc, and preferably zinc. If an optically active product is to be made, the chelating compound should itself be scalemic.

The chelate compound can for example have the formula I or analogue thereof with zinc replaced by another Lewis acid former:

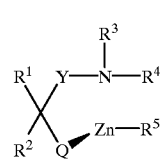

(I)

It is believed that the composition formed between the organozinc compound produced by the process of the first aspect of the present invention and the chelate compound can for example have the formula II or its analogue having another intra-annular Lewis acid former in place of zinc:

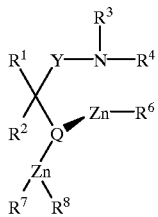
(II)

In these formulae:

Y is methylene or ethylene optionally carrying one or more substituents inert to organozinc compounds;

$R^1$ and $R^2$ are groups inert to organozinc compounds. Typically they are selected from hydrogen and the organic groups which may be present in the organozinc compound produced in the first aspect of the present invention, particularly hydrocarbon groups, such as $C_{1-2}$ alkyl and preferably phenyl, heterocyclyl, ether, thioether and secondary amino, and may be substituted. They may be joined externally to form a ring or rings;

$R^3$ and $R^4$ are independently selected from hydrogen and the organic groups which may be present in the organozinc compound produced in the first aspect of the present invention, particularly hydrocarbon, such as $C_{1-2}$ alkyl, preferably $C_{1-6}$ alkyl, and may together form a ring; or a group of formula —$COR^x$, —$CO_2R^x$, or —$SO_2R^x$ wherein $R^x$ is a $C_{1-6}$ alkyl group. $R^3$ and $R^4$ (except hydrogen) may carry one or more substituents inert to organozinc compounds; either or both of $R^3$ or $R^4$ may carry a substituent —Z—$NR^9R^{10}$ where Z is ethylene or trimethylene optionally carrying one or more substituents inert to organozinc and $R^9$ and $R^{10}$ each independently are as defined for $R^3$ but need not be the same as $R^3$;

$R^5$ can be any of the organic groups which may be present in the organozinc compound produced in the first aspect of the present invention. Note that $R^5$ occurs only in I and is present normally as the product of reacting an organozinc compound with an amino alcohol. Preferably $R^5$ is aryl or heterocyclyl;

$R^6$ can be any of the organic groups which may be present in the organozinc compound produced in the first aspect of the present invention. Note that $R^5$ occurs only in II. It may be the same as $R^5$ in I but may with advantage be lower aliphatic ($C_{1-6}$), since the zinc alkyls leading to such a value for $R^6$ are readily available in a pure state and need not be made by the process of the invention;

$R^7$ and $R^8$ are as defined for the organic groups of the organozinc compound produced in the first aspect of the present invention; and Q represents O, S or a group of formula —$NRYRF$, wherein $R^y$ and $R^z$ are each independently as defined for $R^3$ and $R^4$.

It is believed that some association of molecules of I can take place, but that reaction with $ZnR^7R^8$ reverses such association.

When a group of formula —Z—$NR^9R^{10}$ is present, the nitrogen of —Z—$NR^9R^{10}$ may coordinated to the annular zinc atom.

The composition of matter which may result in the formation of compounds of Formula (II) is believed to be new. Accordingly, a second aspect of the present invention provides a composition of matter obtained by mixing a Lewis acid, a chelator selected from aminoalcohols, aminothiols, diamines or diols, in which the chelating groups are separated by 2 or 3 carbon atoms and an organozinc compound of formula $ZnR^{11}R^{12}$ herein $R^1I$ and $R^{12}$ are each independently organic groups as defined for the organic groups of the organozinc compound produced in the first aspect of the present invention.

The Lewis acid may be an organolithium compound, an organoboron compound or an organotitanium compound, but is preferably an organozinc compound of formula $ZnR^3R^{14}$, wherein $R^{13}$ and $R^{14}$ are each independently organic groups, and can be any of the organic groups which may be present in the organozinc compound produced in the first aspect of the present invention, but provided that the compound $ZnR^{13}R^{14}$ is different from the compound of formula $ZnR^{11}R^{12}$. Preferably $R^{13}$ and $R^{14}$ are each $C_{1-6}$ alkyl groups.

If a composition according to the second aspect of the present invention is to be used to prepare an optically active product, the chelator compound from which the composition is prepared should itself be scalemic.

In the composition of matter according to the present invention, in the organozinc compound of formula $ZnR^{11}R^{12}$, $R^{11}$ and $R^{12}$ are preferably phenyl, tolyl, xylyl or mesityl groups.

The mole ratio of chelator to Lewis acid in the composition at point of mixing is often from 0.1:1 to 1:0.1, commonly from:0.5:1 to 1:0.5 and preferably from 0.8:1 to 1:0.8. The mole ratio of chelator and/or Lewis acid to organozinc compound of formula $ZnR^{11}R^{12}$ is often from 1:1 to 1:100, commonly from 1:5 to 1:50, and preferably from 1:10 to 1:25.

Examples of chelating compounds suitable for use in the compositions of the second aspect of the present invention are those compounds numbered 50–65b in the chapter Organozinc, organocadmium and organomercury reagents, pages 211–229, especially 223–224, of Comprehensive Organic Synthesis, Volume 1, first edition 1991, Pergamon Press. These chelating compounds and also the article by Evans, in Science 1988, 240, 420–426, are incorporated herein by reference and are authority for structures I and II. The chelator is preferably one of cyclohexanediamine bis (triflamide), dimethylaminoisoborneol, α,α-diphenyl-2-pyrollidinemethanol, and especially diethyl or dibutyl-norephedrine. Should other structures be proposed, the compositions are of course still within the scope of the invention.

The compositions according to the second aspect of the present invention preferably additionally comprise a hydrocarbon, most preferably the liquid employed in the process according to the first aspect of the present invention.

Organozinc compounds can be employed as reagents in a number of reactions, particularly in reactions generating asymmetry. However, many organozinc compounds conventionally employed suffer because of the relatively high concentrations of metal halides, which function as contaminant Lewis acids. It is believed that the presence of such a contaminant Lewis acid is undesirable owing to one or more of the mechanisms:

(a) it competes with the organozinc compound for complexation with the catalyst;
(b) it reacts with organozinc compounds to form organozinc halides which are less selective reagents affording substantially lower enantiomeric excess;

(c) it coordinates to the substrate compound and activates it for addition of free organozinc compound affording substantially lower enantiomeric excess; and (d) it catalyses the non-enantioselective reaction at a rate sufficient to substantially lower the purity of the product.

According to a third aspect of the present invention, there is provided a process for the introduction of an organic moiety into a substrate compound wherein the substrate compound is reacted with an organozinc compound prepared according to the process of the first aspect of the present invention.

Preferably, the organozinc compound is employed as a composition according to the second aspect of the present invention.

The substrate compound contains at least one of:

(a) a hetero-atom multiply linked to carbon;

(b) a multiple carbon-carbon bond conjugated with a hetero-atom multiply linked to carbon;

(c) an activated halogen; and (d) an ethylene oxide and at least one organic group as hereinbefore defined.

Category (a) includes especially aldehydes and aldimines. Category (b) includes especially α,β-unsaturated compounds containing such groups or also possibly other electron-withdrawing groups such as $CF_3$, sulphone or nitro. Category (c) includes allyl halides, benzyl halides, aryl halides and acyl halides.

The reaction involving addition of an organozinc compound to a substrate from category (a) is believed to proceeds by way of an intermediate of formula II above in which intra-annular zinc is present if more than one mole of organozinc compound is used per mole of substrate. Since the reaction of II regenerates I the excess of organozinc can be for example 5–25% in molar terms.

A preferred process according to the third aspect of the present invention comprises reacting a prochiral aldehyde or aldimine with either:

a) an organozinc compound prepared by the process of the first aspect of the present invention in the presence of a scalemic chelating compound catalytic for the reaction, preferably an aminoalcohol, diamine, aminothiol or a diol, in which the chelating groups are separated by 2 or 3 carbon atoms; or b) a composition according to the second aspect of the present invention.

Aldehydes and aldimines that can be employed in the process according to the third aspect of the present invention have the formulae:

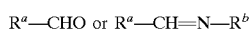

$R^a$—CHO or $R^a$—CH=N—$R^b$ wherein $R^a$ is an aromatic or aliphatic group, particularly an optionally substituted phenyl, pyridyl or thienyl group, and Rb is H or an optionally substituted alkyl, preferably $C_{1-6}$ alkyl, aryl or benzyl group. It will be recognised that to generate a chiral product, the organic group introduced by the organozinc compound should be different from that represented by $R^a$.

Substituents which may substitute the organometallic compounds, organozinc compounds, groups $R^{1-14}$, groups $R^x$, $R^y$, $R^z$, $R^a$ and $R^b$ and Y, especially $R^a$ and $R^b$, are generally selected to be inert under the reaction conditions under the prevailing reaction conditions. Commonly, the substituents are selected from halogen, alkyl, particularly $C_{1-6}$ alkyl, aryl, particularly phenyl, —OR, —OCOR, —COR, —$CO_2R$, —CN, —SH, —SR, —$SO_2R$, —$SO_3R$, —$SONR_2$, —SCSR, —$PR_3$, —POR, —$PO_2R$, —$NR_2$ and $SiR_3$, wherein R represents H or an alkyl, preferably a $C_{1-6}$, alkyl, or aryl, preferably a phenyl, group. When R represents an alkyl or aryl group, further substituents may be present. The substituents may also be selected from metal carbonyl groups, such as iron carbonyl.

In a particular process the substrate is a substituted benzaldehyde, especially halo, particularly chloro, fluoro or bromo ( each 2, 3- or 4), alkoxy, especially $C_{.1}$ alkoxy, (preferably 4-) or trifluoromethyl, or heterocyclic aldehyde such as pyridine-3-aldehyde.

The reaction preferably occurs in the presence of a solvent. Preferably, the solvent has no basic or acidic functional groups present, and is most preferably a hydrocarbon as defined herein for use as the liquid. The mole ratio of organozinc compound to aldehyde or aldimine is often selected to be in the range of from 0.8:1 to 3:1, and is preferably from 1:1 to 1.5:1, based on the number of aldehyde or aldimine functionalities to which an organic moiety is desired to be introduced. Commonly, there is a single such functionality.

The reaction may take place with catalysis by transmetallation, in presence of a compound of a transition metal such at titanium, copper, nickel or palladium. Thus the effective reactant may be a compound of such metal, formed as a distinct component of the reaction mixture or transiently.

The organozinc composition may be introduced as such or formed in a distinct process step or formed transiently in a reaction mixture containing organozinc compound, catalytic chelator compound and substrate compound. If the addition reaction is required, the process preferably comprises the separate steps:

(i) reacting an organozinc compound with the chelating compound;

(ii) reacting the product of (i) with an organozinc compound produced by the process according to the first aspect of the present invention, an organic group, commonly an aromatic group of which is to be added to the substrate; and (iii) reacting the product of (ii) with the substrate.

In this process, step (i) should be controlled to avoid the first organozinc compound from occupying the reactive sites in the chelator which may be occupied by the second organozinc compound if the first organozinc compound does not provide the group to be added to the substrate compound. Such control may be for example by reference to mixing procedures or by allowing sufficient time for redistribution of the first organozinc compound into the ring position.

The processes of the various aspects of the invention are carried out using anhydrous reactants and in anhydrous oxygen-free conditions. When reactant metals other than organozinc compounds are present, carbon dioxide should also be excluded.

In the process of the third aspect, after the reaction with the substrate, the reaction mixture is worked up by procedures established in this branch of technology, usually by reacting it with acid, such as hydrochloric or sulphuric acid and separating the required product as a water-insoluble layer. The temperature is kept low, usually below 20° C., to avoid or limit possible racemisation, although If racemisation is not a problem, higher temperatures may be employed.

The invention is further illustrated by the following examples.

(a) Preparation of D(+) Diethylnorephedrine (D(+) DENE) (1-phenyl-1-hydroxy-2-methyl-2-diethylaminoethane) Materials

| Material | Amt(g) | Strength | Moles | Mol Eq |
|---|---|---|---|---|
| IS, 2R norephedrine | 30.8 | 98% | 0.2 | 1 |
| ethanol | 130 ml | | | |
| potassium carbonate | 55.7 | 99% | 0.4 | 2 |
| iodoethane | 78 | 99% | 0.5 | 2.5 |

Equipment

An oven dried 500 ml multinecked RBQF with thermometer, pressure equalising addition funnel with nitrogen bubbler and PTFE paddle stirrer.

Procedure

The dry glassware was purged with nitrogen. The potassium carbonate, norephedrine and absolute ethanol were charged together and stirred while heating to reflux at 70° C. to give a thin pale yellow slurry. The iodoethane was mixed with ethanol, charged to the addition funnel and then added dropwise to the reaction mixture over 3 hours. Samples were taken and analysed by GC at approximately hourly intervals. From the rate of reaction it was decided to continue refluxing overnight. After 19 hours the reaction mixture was cooled to ambient temperature and the inorganic solids filtered using a sintered glass filter. The solids were slurry washed with two 25 ml portions of ethanol. The filtrates were combined and stripped of solvent on the rotary evaporator at 40° C. and 20 mmHg to give a creamy white oily solid, weight 48.6 g. This solid was dissolved in 150 ml methylene chloride and washed with 75 ml water. The pH of the aqueous phase was increased from 10 to 11 using dilute sodium hydroxide and the phases stirred together then allowed to separate. The well separated organic phase was run-off and the aqueous phase rewashed twice with 25 ml methylene chloride. The combined organics were dried over solid anhydrous magnesium sulphate, filtered over paper and concentrated to dryness on a rotary evaporator to give 50.3 g of an off-white oil, part of which solidified overnight. The insolubles were separated using a sintered glass filter and washed with two 25 ml portions of hexane. The washings and filtrates were combined and the solvent was stripped on the rotary evaporator to give 36.3 g of a pale yellow oil. By GC this gave a strength based on area % of 96.7%, that is 85% yield based on norephedrine. The optical purity was determined by chiral HPLC to be 396.7%.

(b) Preparation of D(+) di-n-butyl norephedrine D(+) DBNE

The same procedure was followed using n-butyl bromide.

EXAMPLE 1

Preparation of Diphenylzinc via Phenyl-magnesium Bromide

| Material | Actual Wt(g) | 100% Wt(g) | Gram Moles | Molar Ratio |
|---|---|---|---|---|
| Anhydrous zinc bromide | 11.37 | 11.26 | 0.05 | 1.0 |
| Phenylmagnesium bromide (3.0M solution in diethylether) | 33.3 ml | 18.13 | 0.1 | 2.0 |
| Diethylether (dried over Na) | 75 ml | | | |
| Toluene | 100 ml | | | |
| Tetrahydrofuran (dried) | 50 ml | | | |

-continued

| Material | Actual Wt(g) | 100% Wt(g) | Gram Moles | Molar Ratio |
|---|---|---|---|---|
| D(+)DENE | 0.64 | 0.62 | 0.003 | 0.06 |
| Nicotinaldehyde (pyridine-3-aldehyde) | 5.4 | 5.35 | 0.05 | 1.0 |
| Hydrochloric acid (6M HCl) | 50 ml | | | |
| Diethylether | 100 ml | | | |

Apparatus

An oven dried, multinecked 250 ml round bottom Quickfit (RTM) flask (RBQF) fitted with a PTFE paddle stirrer, thermometer, reflux condenser with nitrogen bubbler and a port with a SubaSeal (RTM) septum cap was used.

To filter the inorganic solids the condenser was replaced by an in-line No 3 sintered glass filter connected with flexible PTFE tubing under inert atmosphere. The filtrates were collected in a second dry 250 ml RBQF fitted with PTFE paddle stirrer, pressure equalising addition funnel, thermometer and inlet port from the in-line filter, all under an inert nitrogen atmosphere.

Method (a) Preparation of Diphenylzinc

The zinc bromide was dried overnight at 120° C. and about 14 mmHg, then dissolved in 75 ml dry diethylether (stored over Na) in a nitrogen atmosphere in the flask cooled to 4° C. using an ice bath. The inert atmosphere was re-established and the phenylmagnesium bromide introduced from a 'Sure-Seal' (RTM) bottle via the septum using a dry 20 ml syringe. The reaction mixture was held below 10° C. during this addition, then allowed to warm to room temperature (19° C.) and stirred for 30 min. The mixture at the end of the addition was a grey/brown solution with a granular white precipitate. The reflux condenser was re-set for distillation and the mixture heated to 76° C.; 74 ml ether were distilled off at 39° C. atmospheric pressure. 100 ml of dry toluene were then added by syringe, upon which the grey crystalline slurry lightened in colour. Distillation was continued until the head temperature reached 113° C.; then the mixture was cooled to 21° C. and allowed to stand overnight. A further 50 ml of toluene were added, then the mixture warmed to 105° C. and filtered using the apparatus described above. The filter cake was blown dry with nitrogen. The filtrate was a pale yellow solution of substantially pure diphenylzinc (88 mol % Zn, 2 mol % Mg). The flask was sealed and stored in a refrigerator.

(b) Preparation of Phenyl-3-Pyridyl Carbinol (i) Invention Process

To the pale yellow filtrates the D(+)DENE was added against a counter-current of nitrogen. The temperature rose from 16 to 31° C. and was then cooled back to 17° C. To the resulting solution of complexed reagent II 40 ml of dry THF were added in one portion by syringe; the temperature rose to 30° C. The nicotinaldehyde in 10 g THF was charged to the addition funnel and added dropwise to the mixture at 21° C. over 6 hours. During this period samples were taken and, after quenching in acid, neutralising and extracting with methylene chloride, analysed by chiral capillary GC (see below). After 213 of the aldehyde had been added the GC showed accumulation of aldehyde and the addition was thus stopped.

Work-up was by addition of the HCl to the chilled reaction mixture, keeping the temperature below 20° C. The organic layer was separated and washed with 25 ml water. The aqueous layer was washed with 25 ml diethylether and 25 ml methylene chloride. The aqueous phases were combined and neutralised to pH 6/7 with sodium hydroxide solution in the presence of 50 ml methylene chloride. The organic phase was separated and the aqueous layer washed with a further 25 ml of methylene chloride. This was combined with the previous extract, then distilled on a rotary evaporator to give 8.7 g of a pale yellow viscous oil which solidified on cooling.

The product was analysed by GC and shown to be 88.5% strength based on area %. The optical purity was determined by both chiral shift HNMR (73% ee) and chiral capillary electrophoresis (73.4% ee).

(ii) Comparative Runs

Run (i) was repeated twice with the difference that the diphenylzinc was a commercially obtained sample purified by sublimation and that the diphenylzinc, D(+)DENE and aldehyde were reacted together in a single stage, and (for one of these runs) magnesium chloride 6 mol % on the aldehyde was present. The results were:

|  | % Yield | % e.e. |
|---|---|---|
| No MgCl$_2$ | 86 | 54 |
| MgCl$_2$ | 47 | 18 |

EXAMPLE 2

Example 1(b) was repeated but using 0.06 mol of diethylzinc, 0.06 mol of D(+)DENE and 1 mol of diphenytzinc. The diethylzinc and DENE were reacted together before adding the diphenylzinc. The products were phenylpyridylcarbinol 36% yield, 46% e.e.

pyridylethyl carbinol 14% yield

Comparison 3:Use of Schienk Procedure

Materials

| Material | Actual Wt(g) | 100% Wt(g) | Gram Moles | Molar Ratio |
|---|---|---|---|---|
| Zinc chloride (1.0M solution in diethylether) | 20 ml | 2.73 | 0.02 | 1.0 |
| Phenylmagnesium bromide (3.0M solution in diethylether) | 13.3 ml | 7.25 | 0.04 | 2.0 |
| Tetrahydrofuran (THF) (distilled and dried over molecular sieves) | 60 ml | | | |
| Tetrahydrofuran (dried) | 50 ml | | | |
| 1,4-dioxane | 7.05 | 7.05 | 0.08 | 4.0 |
| D(+)DBNE | 0.324 | 0.316 | 0.0012 | 0.06 |
| Nicotinaldehyde | 2.16 | 2.14 | 0.02 | 1.0 |
| Hydrochloric acid (6M) | 20 ml | | | |

Apparatus

As in Example 1

Method (a) Preparation of Diphenylzinc

The zinc chloride solution was charged to the flask by syringe and diluted with 60 ml THF all under a nitrogen atmosphere. The stirrer was started and phenylmagnesium bromide introduced using a dry 20 ml syringe dropwise over 5 min initially forming a precipitate which dissolved by the end of the addition. The reaction mixture was held at 20–25° C. during addition and stirred for a total of 2 hours. The dioxan was then added by syringe causing a fine, white solid to precipitate. The slurry was stirred a further 45 min at 25° C., then filtered via the in-line sintered glass filter. The filter cake was washed with 10 ml THF and blown dry with nitrogen. The filtrate was a pale yellow solution in THF of diphenylzinc (57 mol % Zn, 10.2 mol % Mg). The flask was sealed and stored in a refrigerator.

(b) Preparation of Phenyl-3-Pyridyl Carbinol

To a sample of the filtrates at 5° C. a premixed solution of D(+)DBNE, nicotinaldehyde and 10 ml THF was added dropwise over 10 min. By the end of the addition a light, white slurry had formed. The reaction mixture was warmed to ambient temperature, stirred 18 hours, then cooled to 7° C. and quenched with dilute hydrochloric acid. The organic layer was separated and washed with 25 ml water. The aqueous layer was washed with 25 ml diethylether and 25 ml methylene chloride. The aqueous phases were combined and neutralised to pH 6/7 with sodium hydroxide solution in the presence of 50 ml methylene chloride. The organic phase was separated and the aqueous layer washed with a further 25 ml methylene chloride. This was combined with the previous extract and distilled on a rotary evaporator to give 4.11 g of a pale yellow solid. The product was analysed by GC and shown to be 74.1% strength based on area %. This gives a yield of 84.5% based on the aldehyde. The optical purity was determined by both chiral shift HNMR and chiral HPLC and found to be 0% ee, i.e. racemic.

EXAMPLE 4

Preparation of Diphenyizinc Via Phenyllithium

Materials

|  | MWt | Qnty | 100% Wt(g) | Moles |
|---|---|---|---|---|
| Anhydrous zinc chloride | 136.6 | 2.78 g | 2.73 | 0.02 |
| Phenyllithium (1.8M solution in 30:70 cyclohexane:diethylether) | 84.05 | 22.2 ml | 3.36 | 0.04 |
| Diethylether (dried over Na) | | 75 ml | | |
| Tetrahydrofuran (dried over Na) | | 50 ml | | |
| D(+)DENE | 207 | 0.256 g | 0.248 | 0.0012 |
| Nicotinaldehyde | 107 | 2.16 g | 2.14 | 0.02 |
| Hydrochloric acid | | 50 ml | | |
| Methylene chloride | | 75 ml | | |

Apparatus

As in Example 1

Method (a) Preparation of Diphenylzinc

The zinc chloride was dried overnight at 120° C. and __14 mmHg and dissolved in 75 ml of dry diethylether at reflux under nitrogen. The solution was cooled to 3° C. using an ice bath placed under the flask. The phenyllithium was charged by syringe via a septum into the addition funnel, and then added dropwise over 15 min to the zinc chloride solution. Initially a white precipitate was formed which became darker and heavier and after 15 min further stirring was difficult. The mixture was heated under reflux (39° C.) using an oil bath for 2½ hours, during which the solid turned dark grey. The slurry was filtered hot using the in-line filter. The filter-cake was blown dry using nitrogen. The filtrates were somewhat cloudy due to an insoluble brown oil; this was allowed to settle and removed by pipette. The ether solution was diluted with THF, cooled to >5° C. using an ice bath and stored in a refrigerator.

(b) Preparation of Phenyl-3-Pyridyl Carbinol

To a sample of the solution was added the solid D(+) DENE, followed by the solid aldehyde. The resulting cloudy yellow solution was warmed to 20° C., during which a white precipitate formed, then stirred overnight. 17 hours later the reaction mixture was worked-up by adding 50 ml methylene chloride and then slowly 50 ml hydrochloric acid maintaining the temperature below 15° C. The organic layer was separated and washed with 25 ml water. The washing water combined with the aqueous layer was neutralised to pH 6/7 using sodium hydroxide solution and extracted twice with methylene chloride, 50 ml then 25 ml. The organic extracts were combined and distilled on a rotary evaporator to give 4.31 g of a viscous, dark straw-coloured oil.

The oil was analysed by GC and shown to be 86% strength, based on area %. This equates to 3.7 g @ 100% and gives a 100% yield based on the aldehyde. The product was characterised by HNMR:C$\underline{H}$OH,1H,5.83s; Ar$\underline{H}$ 7.24, 5H; Ar $\underline{H}$:Ha7.37,J=5.26,7.21; Ar$\underline{H}$:Hb7.80,J=8.0; Ar $\underline{H}$:Hc8.55,J=1.37,3.89; Ar$\underline{H}$:Hd8.77,J=1.8. The optical rotation is $a_{20}$=−13.6 c=2.0 $CH_2Cl_2$. The optical purity was measured by chiral shift 1HNMR and chiral GC (60% ee)and chiral capilliary electrophoresis as 60.6% ee.

EXAMPLE 5

Preparation of Diphenylzinc By Reaction of Phenyllithium With Zinc Bromide

Example 4(a) was repeated using zinc bromide in place of zinc chloride and in process conditions varied as follows:

(i) reaction mixture allowed to stand overnight at 0–5° C., then refluxed at 41° C. for 2 hours;

(ii) reaction mixture refluxed 1 hour at 43° C., then diluted with toluene (25% w/w); the ether was distilled off and reflux resumed at 82° C., to a total reflux time of 3 hours;

(iii) the zinc bromide was added as a solution (10.8% w/w) in toluene; refluxing was at 90° C. and was carried on for 16 hours.

The resulting solutions of diphenylzinc were reacted with substituted benzaldehydes and the products analysed for-yield and enantiomeric excess. Results are shown in the Table.

TABLE

| Source of diphenylzinc | Benzaldehyde substituent | Yield % w/w on the aldehyde | Enantiomeric excess, % |
|---|---|---|---|
| i | o-$CF_3$ | 80.6 | 0 |
| ii | o-$CF_3$ | 83.3 | 43.5 |
| ii | m-$CF_3$ | 94.4 | 55.8 |
| iii | p-$CF_3$ | 100.0 | 65.7 |

By comparison with Example 4 it appears that the solubility of lithium bromide in the ether-cydohexane mixture is too great to give diphenylzinc pure enough to afford enantiomeric excess. However, when as in (ii) and (iii), the diphenylzinc is brought into ether-free solution, the solubility of lithium bromide is low enough to give diphenylzinc capable of substantial enantiomeric excess.

EXAMPLE 6

Reaction of Diphenylzinc, Itself Prepared From Phenylmagnesiumbromide and Zinc Bromide, With Substituted Benzaldehydes Anhydrous zinc bromide (6.82 g) was charged to a dry, stirred 250 ml flask filled with nitrogen. Dried diethylether (75 ml) was added and the slurry heated to reflux until a homogenous solution. A 3molar ethereal solution of phenyl-magnesium bromide (20 ml) was slowly added. Solvent was distilled from the reaction mixture at ambient pressure, whilst maintaining a constant volume by addition of toluene until a distillate temperature of at least 108° C. was reached. The hot slurry was screened under a nitrogen atmosphere using an in-line sintered glass filter. The filtrates were received into a dry, stirred 250 ml flask and cooled to ambient temperature. L(−) diethyinorephedrine was added and the substituted benzaldehyde charged from a dropping funnel. The reaction mixture was stirred for a total of 12 hours then cooled on an ice bath and quenched by addition of dilute hydrochloric acid. The organic layer was separated, washed with an equal volume of water and concentrated to yield a crude product. Unless indicated otherwise, weights of products are on crude material. For characterisation purposes materials were further purified by recrystallisation. Optical purities were measured by chiral GC and chiral shift HNMR.

| R | catalyst weight (g) | product weight (g) | ee (%) | $a_{20}$ | HNMR & Mass Spectra |
|---|---|---|---|---|---|
| o-$CF_3$ | 0.76 | 3.8 | 20 | +12.67 c = 2.05 | C$\underline{H}$OH, 1H, 6.20s; Ar$\underline{H}$7.1–7.60, 9H 252, 233, 214, 195, 183, 166, 153, 105, 77, 51 |
| m-$CF_3$ | 0.76 | 3.6 | 84 | +25.05 c = 2.83 | C$\underline{H}$OH, 1H, 5.78s; Ar$\underline{H}$7.1–7.65, 9H 252, 233, 214, 195, 183, 166, 153, 105, 77, 51 |
| p-$CF_3$ | 0.91 | 3.5 | 24 | +9.38 c = 1.7 | C$\underline{H}$OH, 1H, 5.78s; Ar$\underline{H}$7.26 5H Ar$\underline{H}$, AB, 7.45, 4H, J = 8.46, 9.83 Hz 252, 233, 214, 195, 183, 166, 153, 105, 77, 51 |
| o-Cl | | | | | C$\underline{H}$OH, 1H, 6.10s; Ar$\underline{H}$7.1–7.90, 9H |
| m-Cl | 0.76 | 3.3 | 23 | +6.45 c = 2.0 | C$\underline{H}$OH, 1H, 5.59s; Ar$\underline{H}$7.05–7.28, 9H 218.5, 183, 166, 153, 105, 77, 51 |
| p-Cl | 0.37 | 1.3 | 14 | +3.49 c = 2.0 | C$\underline{H}$OH, 1H, 5.76s; Ar$\underline{H}$7.25–7.37, 9H 218.5, 183, 166, 153, 139, 113, 105, 77, 51 |
| o-$OCH_3$ | 0.32 | 1.7 | +/− | | |
| m-$OCH_3$ | 0.64 | 4.1 | 41 | −4.00 c = 2.0 | C$\underline{H}$OH, 1H, 5.79s; Ar$\underline{H}$6.78–7.45, 9H; OC$\underline{H}_3$, 3.80s, 3H |
| p-$OCH_3$ | 0.37 | 0.9 | +/− | | C$\underline{H}$OH, 1H, 5.74s; Ar$\underline{H}$6.8–7.4, 9H; OC$\underline{H}_3$, 3.76s, 3H 214, 213, 197, 181, 167, 153, 135, 105, 77, 51 |

EXAMPLE 7

Reaction of Diphenylzinc, Itself Prepared From Phenyllithium and Zinc Bromide, With Substituted Benzaldehydes Anhydrous zinc bromide (5.73 g) was charged to a dry, stirred 250 ml flask filled with nitrogen. Dried diethylether (52 ml) was added and the slurry heated to reflux until a homogenous solution. The solution was cooled to ambient temperature and a 1.8 molar cyclohexane/ether (7:3) solution of phenyllithium (28 ml) (Aldrich) was slowly added from a dropping funnel over 2 hours. The reaction mixture was heated to reflux for 1 hour then toluene (30 ml) added. Solvent was distilled at ambient pressure, from the reaction until the distillate temperature reached at least 85° C. The slurry was cooled to ambient temperature, allowed to settle and the liquid carefully decanted using a syringe and needle. This solution was charged to a dry, stirred 250 ml flask, and cooled to 5° C. L(−) diethylnorephedrine (0.124 g) and tetrahydrofuran (2 ml) was added and the substituted benzaldehyde (0.00715 moles) in tetrahydrofuran (8 ml) charged from a dropping funnel over 2 hours. The reaction mixture was stirred for a total of 12 hours then cooled on an ice bath and quenched by addition of dilute hydrochloric acid. The organic layer was separated, washed with an equal volume of water and concentrated to yield a crude product. Unless indicated otherwise, weights of products are on crude material. For characterisation purposes materials were further purified by recrystallisation. Optical purities were measured by chiral GC and chiral shift HNMR.

| R | product weight (g) | ee (%) | $a_{20}$ | HNMR & Mass Spectra |
|---|---|---|---|---|
| o-CF$_3$ | 1.5 | 44 | (+) | C$\underline{H}$OH, 1H, 6.20s; Ar$\underline{H}$7.1–7.60, 9H 252, 233, 214, 195, 183, 166, 153, 105, 77, 51 |
| m-CF$_3$ | 1.7 | 56 | +7.57 c = 2.4 | C$\underline{H}$OH, 1H, 5.78s; Ar$\underline{H}$7.1–7.65, 9H 252, 233, 214, 195, 183, 166, 153, 105, 77, 51 |
| p-CF$_3$ | 1.8 | 66 | +33.5 c = 1.5 | C$\underline{H}$OH, 1H, 5.78s; Ar$\underline{H}$7.26 5H Ar$\underline{H}$, AB, 7.45, 4H, J = 8.46, 9.83 Hz 252, 233, 214, 195, 183, 166, 153, 105, 77, 51 |

EXAMPLE 8

Reaction of Diphenylzinc, Itself Prepared From Phenyllithium and Zinc Bromide, With Substituted Benzaldehydes Anhydrous zinc bromide (10.45 g) was charged to a dry, stirred 250 ml flask filled with nitrogen. Dried toluene (97 ml) was added and the slurry heated to 80° C. until a homogenous solution. The solution was cooled to 0–5° C. and a 1.8 molar cyclohexaneether (7:3) solution of phenyllithium (50.5 ml) (Aldrich) was slowly added from a dropping funnel over 2 hours. The reaction mixture was heated to reflux for 12 hour then cooled to ambient temperature, allowed to settle and the liquid carefully decanted using a syringe and needle into a storage jar and kept at ambient temperature as a stock solution. Diphenylzinc solution (30 ml) was charged to a dry, stirred 250 ml flask, and cooled to 5° C. L(−) diethyinorephedrine (0.124 g) and tetrahydrofuran (2 ml) was added and the substituted benzaldehyde (0.00715moles) in tetrahydrofuran (8 ml) charged from a dropping funnel over 2 hours. The reaction mixture was stirred for a total of 12 hours then cooled on an ice bath and quenched by addition of dilute hydrochloric acid. The organic layer was separated, washed with an equal volume of water and concentrated to yield a crude product. Unless indicated otherwise, weights of products are on crude material. For characterisation purposes materials were further purified by recrystallisation. Optical purities were measured by chiral GC and chiral shift HNMR.

| R | product weight (g) | ee (%) | $a_{20}$ | HNMR & Mass Spectra |
|---|---|---|---|---|
| o-Cl | 2.4 | 54 | −1.39 c = 2.15 | C$\underline{H}$OH, 1H, 6.10s; Ar$\underline{H}$7.1–7.90, 9H 218.5, 183, 165, 152, 139, 112, 105, 77, 51 |
| m-Cl | 1.8 | 72 | +6.59 c = 2.3 | C$\underline{H}$OH, 1H, 5.59s; Ar$\underline{H}$7.05 –7.28, 9H 218.5, 183, 165, 152, 139, 111, 105, 77, 51 |
| p-Cl | 1.8 | 28 | +9.48 c = 2.74 | C$\underline{H}$OH, 1H, 5.76s; Ar$\underline{H}$7.25–7.37, 9H 218.5, 183, 166, 165, 152, 139, 111, 105, 77, 51 |
| o-Br | 2.0 | 28 | −5.16 c = 2.3 | 263, 183, 165, 152, 105, 77, 51 |
| m-Br | 3.6 | 40 | +10.85 c = 2.2 | C$\underline{H}$OH, 1H, 5.80s; Ar$\underline{H}$7.15–8.09, 9H 263, 183, 166, 153, 105, 77, 51 |
| p-Br | 2.0 | 24 | +6.63 c = 2.11 | C$\underline{H}$OH, 1H, 5.76s; Ar$\underline{H}$7.2–7.65, 9H 263, 183, 166, 153, 105, 77, 51 |
| o-OCH$_3$ | 1.9 | +/− | −1.66 c = 2.4 | 214, 198, 183, 165, 151, 135, 105, 77, 51 |
| m-OCH$_3$ | 1.7 | 68 | −7.49 c = 2.1 | C$\underline{H}$OH, 1H, 5.79s; Ar$\underline{H}$6.78–7.45, 9H OC$\underline{H}_3$, 3.80s, 3H 214, 197, 183, 181, 165, 152, 135, 105, 77, 51 |
| p-OCH$_3$ | 1.9 | 1 | 0.00 c = 2.8 | C$\underline{H}$OH, 1H, 5.74s; Ar$\underline{H}$6.8–7.4, 9H OC$\underline{H}_3$, 3.76s, 3H 214, 197, 181, 165, 151, 135, 105, 77, 51 |

EXAMPLE 9

Reaction of Diarylzinc, Itself Prepared From Arylmagnesiumbromide and Zinc Bromide, With Benzaldehyde Magnesium powder (50mesh)(1.23 g), anhydrous zinc bromide (5.75 g) and tetrahydrofuran (50 ml) were charged to a dry stirred 250 ml flask filled with nitrogen. The mixture was heated to reflux at 65° C. and a solution of substituted arylbromide (0.05 moles) in tetrahydrofuran (10 ml) was added dropwise. The mixture was maintained at reflux for a further 2 hours. Toluene (100 ml) was added to the mixture and solvent distilled at ambient pressure, whilst maintaining a constant volume by addition of toluene until a distillate temperature of at least 108° C. was reached. The hot slurry was screened under a nitrogen atmosphere using an in-line sintered glass filter. The filtrates were received into a dry, stirred 250 ml flask and cooled to 1° C. L(−) diethyinorephedrine (0.33 g) in tetrahydrofuran (15 ml) was added and benzaldehyde (2.7 g) in tetrahydrofuran (5 ml) charged from a dropping funnel. The reaction mixture was warmed to ambient temperature, stirred for a total of 12 hours then cooled on an ice bath and quenched by addition of dilute hydrochloric acid. The organic layer was separated, washed with an equal volume of water and concentrated to yield a crude product. Unless indicated otherwise, weights of products are on crude material. For characterisation purposes materials were further purified by recrystallisation. Optical purities were measured by chiral GC and chiral shift HNMR.

| R | product weight (g) | ee (%) | HNMR & Mass Spectra |
|---|---|---|---|
| o-CH$_3$ | 3.8 | | |
| m-CH$_3$ | 5.1 | | |
| p-CH$_3$ | 1.8 | | |
| o-OCH$_3$ | 1.7 | +/− | 214, 198, 183, 165, 151, 135, 105, 77, 51 |
| m-OCH$_3$ | 4.1 | 40 | C$\underline{H}$OH, 1H, 5.79s; Ar$\underline{H}$6.78–7.45, 9H OC$\underline{H}_3$, 3.80s, 3H 214, 197, 183, 181, 165, 152, 135, 105, 77, 51 |
| p-OCH$_3$ | 3.3 | | C$\underline{H}$OH, 1H, 5.74s; Ar$\underline{H}$6.8–7.4, 9H OC$\underline{H}_3$, 3.76s, 3H 214, 197, 181, 165, 151, 135, 105, 77, 51 |
| m-CF$_3$ | 6.2 | 8 | C$\underline{H}$OH, 1H, 5.78s; Ar$\underline{H}$7.1–7.65, 9H 252, 233, 214, 195, 183, 166, 153, 105, 77, 51 |

EXAMPLE 10

Preparation of Dibutylzinc Prepared From Butylmagnesiumchloride and Zinc Bromide Anhydrous zinc bromide (8.6 g) was charged to a dry, stirred, 250 ml flask filled with nitrogen. Dried diethylether (100 ml) was added and the slurry heated to reflux until a homogenous solution. A 2 molar ethereal solution of butylmagnesium chloride (37.5 ml) was slowly added. The reaction mixture was refluxed for a further 3 hours. Solvent was distilled from the reaction mixture at ambient pressure, whilst maintaining a constant volume by addition of toluene until a distillate temperature of at least 108° C. was reached. The hot slurry was screened under a nitrogen atmosphere using an in-line sintered glass filter.

EXAMPLE 11

Reaction of Diphenylzinc, Itself Prepared From Phenylmagnesiumbromide and Zinc Bromide, With Acetaldehyde Anhydrous zinc bromide (11.37 g) was charged to a dry, stirred 250 ml flask filled with nitrogen. Dried diethylether (75 ml) was added and the slurry heated to reflux until a homogenous solution. A 3molar ethereal solution of phenylmagnesium bromide (33.3 ml) was slowly added. Solvent was distilled from the reaction mixture at ambient pressure, whilst maintaining a constant volume by addition of toluene until a distillate temperature of 110° C. was reached. The hot slurry was screened under a nitrogen atmosphere using an in-line sintered glass filter. The filtrates were received into a dry, stirred 250 ml flask and cooled to −5° C. D(+) diethyinorephedrine (0.64 g) was added and the acetaldehyde (2.2 g) in toluene (5 ml) charged from a dropping funnel. The reaction mixture was warmed to ambient temperature, stirred for a total of 12 hours, then cooled on an ice bath and quenched by addition of dilute hydrochloric acid. The organic layer was separated, washed with an equal volume of water and concentrated to yield a crude product (4.62 g). This was further purified by chromatography to give 3.86 g (R)phenylethanol of 17% ee, measured by chiral GC. The product was identified by gas chromatographic comparison with authenticated material.

EXAMPLE 12

Reaction of O-Di(1',1',1'-Trifluorotolyl)Zinc, Itself Prepared From O-(1',1',1'-Trifluorotolyl)Lithium and Zinc Bromide, With 3-Nicotinaldehyde benzotrifluoride (14.8 g) and n-hexane (50 ml) were charged to a dry, stirred, 250 ml flask filled with nitrogen and cooled to 4° C. A 1.6 molar hexane solution of n-butyllithium (68.75 ml)(Aldrich) was charged by syringe and needle. This solution was heated to reflux for 18 hours, then cooled to ambient temperature. A solution of anhydrous zinc chloride (6.95 g) in diethylether (100 ml) was added and the slurry heated to 43° C. Solvent was distilled at ambient pressure, from the reaction until the distillate temperature reached at least 108° C. The hot slurry was screened under a nitrogen atmosphere using an in-line sintered glass filter. The filtrates were received into a dry, stirred 250 ml flask and cooled to ambient temperature. D(+) diethyinorephedrine (0.64 g) and 3-nicotinaldehyde were charged from a dropping funnel. The reaction mixture was stirred for a total of 72 hours then cooled on an ice bath and quenched by addition of dilute hydrochloric acid. The organic layer was separated, washed with an equal volume of water and concentrated to yield a crude product. The crude product was shown by GC/mass spec to contain 6% of the desired product of 49% ee.

EXAMPLE 13

Reaction of Diphenylzinc, Itself Prepared From Phenylmagnesiumbromide and Zinc Bromide, With P-1',1',1'-Trifluoromethylbenzaldehyde Using S-(−)-a,a-Diphenyl-2-Pyrollidinemethanol Catalyst Anhydrous zinc bromide (6.82 g) was charged to a dry, stirred 250 ml flask filled with nitrogen. Dried diethylether (75 ml) was added and the slurry heated to reflux until a homogenous solution. A 3molar ethereal solution of phenylmagnesium bromide (20 ml) was slowly added. Solvent was distilled from the reaction mixture at ambient pressure, whilst maintaining a constant volume by addition of toluene until a distillate temperature of at least 108° C. was reached. The hot slurry was screened under a nitrogen atmosphere using an in-line sintered glass filter. The filtrates were received into a dry, stirred 250 ml flask and cooled to 2° C. S-(−)-a,a-diphenyl-2-pyrollidinemethanol (0.912 g) (Aldrich) was added and p-1',1',1'-trifluoromethylbenzaldehyde (2.61 g) charged from a dropping funnel. The reaction was warmed to ambient temperature, stirred for a total of 16 hours then cooled on an ice bath and quenched by addition of dilute hydrochloric acid. The organic layer was separated, washed with an equal volume of water and concentrated to yield a crude product. Weight of crude product (3.94 g). Chiral GC showed the product to be 24% ee. HNMR and mass spec. confirmed the identity of the product.

What is claimed is:

1. A process for the preparation of an organozinc compound comprising an aromatic moiety by reaction between a zinc chloride, bromide or iodide and an organometallic compound of another metal comprising an aromatic moiety and a metal selected from the group consisting of aluminum, boron, tin, copper, cerium, cadmium, mercury and the alkaline earth metals, thereby producing a reaction product comprising an organozinc compound and a halide salt of the other metal, the reaction product being contacted with a liquid in which the organozinc compound is soluble and the halide salt of the other metal is of low solubility, and separating the halide salt of the other metal from the liquid, characterised in that the liquid is a hydrocarbon.

2. A process according to claim 1, wherein the hydrocarbon is selected from hexane, cyclohexane, toluene, xylene and mesitylene.

3. A process according to claims 1 or 2, wherein the organometallic compound of another metal is an organomagnesium halide.

4. A process according to claim 1, wherein the reaction between the zinc chloride, bromide or iodide and the organometallic compound of another metal takes place in the presence of a solvent having a lower boiling point than the hydrocarbon with which the reaction product is contacted.

5. A process according to claim 1, wherein at least one of the organic group in the organozinc compound produced is an aromatic groups selected from the group consisting of phenyl, naphthyl, furyl, pyridyl, quinolyl, thienyl and benzyl groups, each of which may be optionally substituted.

6. A process according to claim 5, wherein the organic groups in the organozinc compound produced are optionally substituted phenyl groups.

7. A composition of matter obtained by mixing a Lewis acid, a chelator selected from aminoalcohol, aminothiol, diamine or diol, in which the chelating groups are separated by 2 or 3 carbon atoms and an organozinc compound of formula $ZnR^{11}R^{12}$ wherein $R^{11}$ and $R^{12}$ are each independently organic groups, provided that at least one of $R^{11}$ and $R^{12}$ comprises an aromatic moiety.

8. A composition according to claim 7, wherein the mole ratio of chelator to Lewis acid in the composition at point of mixing is from 0.1:1 to 1:0.1.

9. A composition according to claim 7, wherein the mole ratio of chelator to Lewis acid in the composition at point of mixing is from 0.8:1 to 1:0.8.

10. A composition according to claims 7 or 8, or 9 wherein the mole ratio of chelator and/or Lewis acid to organozinc compound of formula $ZnR^{11}R^{12}$ is from 1:1 to 1:100.

11. A process for the introduction of an organic moiety into a substrate compound wherein the substrate compound is reacted with an organozinc compound prepared by reacting a zinc chloride, bromide or iodide and an organometallic compound of another metal comprising an aromatic moiety, thereby producing a reaction product comprising an organozinc compound and a halide salt of the other metal, the reaction product being contacted with a liquid hydrocarbon in which the organozinc compound is soluble and the halide salt of the other metal is of low solubility, and separating the halide salt of the other metal from the liquid hydrocarbon.

12. A composition according to claims 7, 8 or 9, wherein the mole ratio of chelator and/or Lewis acid to organozinc compound of formula $ZnR^{11}R^{12}$ is 1:10 to 1:25.

13. A composition according to claim 11, wherein the composition comprises a hydrocarbon selected from the group consisting of hexane, cyclohexane, toluene, xylene or mesitylene.

14. A composition according to claim 7, wherein the composition comprises a hydrocarbon.

15. A process according to claim 14, wherein the substrate is an aldehyde or aldimine of formulae:

$$R^a\text{---CHO or } R^a\text{---CH}=\text{N---}R^b$$

wherein $R^a$ is an aromatic or aliphatic group, and $R^b$ is H or an optionally substituted alkyl group.

16. A process according to claim 15 wherein the organic group introduced by the organozinc compound is different from that represented by $R^a$ thereby producing a chiral product.

17. A process according to claim 16, wherein a scalemic chelating compound is employed.

18. A process according to any one of claims 15 to 17, wherein the aldehyde is an optionally substituted benzaldehyde or an optionally substituted heterocyclic aldehyde.

19. A process according to any one of claims 15 to 17 wherein $R^b$ is a $C_{1-6}$ alkyl, aryl or benzyl group.

20. A process according to any one of claims 15 to 17 wherein $R^a$ is an optionally substituted phenyl, pyridyl or thienyl group.

21. A process for the preparation of an organozinc compound comprising an aromatic moiety and a non-aromatic moiety by reaction between a zinc chloride, bromide or iodide and either (a) an organometallic compound of a metal other than zinc comprising an aromatic moiety and a non-aromatic moiety or (b) an organometallic compound of a metal other than zinc comprising an aromatic moiety and an organometallic compound of a metal other than zinc comprising a non-aromatic moiety, thereby producing a reaction product comprising an organozinc compound and a halide salt of the metal other than zinc, the reaction product being contacted with a liquid in which the organozinc compound is soluble and the halide salt of the metal other than zinc is of low solubility, and separating the halide salt of the metal other than zinc from the liquid, characterised in that the liquid is a hydrocarbon.

22. A process according to claim 21, wherein the hydrocarbon is selected from hexane, cyclohexane, toluene, xylene and mesitylene.

23. A process according to claims 21 or 22, wherein the organometallic compound of a metal other than zinc is an organomagnesium halide, an organolithium compound or an organolithium halide.

24. A process according to claim 21, wherein the reaction of the zinc chloride, bromide or iodide and the organometallic compound of a metal other than zinc takes place in the presence of a solvent having a lower boiling point than the hydrocarbon with which the reaction product is contacted.

25. A process according to claim 21, wherein the aromatic moiety of the organozinc compound produced is an aromatic group selected from the group consisting of phenyl, naphthyl, furyl, pyridyl, quinolyl, thienyl and benzyl groups, each of which may be optionally substituted.

26. A process according to claim 25 wherein the aromatic moiety of the organozinc compound produced is an optionally substituted phenyl group.

27. A process according to claims 21 or 22 wherein the organometallic compound of a metal other than zinc comprising an aromatic moiety is an optionally substituted phenyl magnesium halide, an optionally substituted phenyl lithium or an optionally substituted phenyl lithium halide.

28. A process according to claims 21 or 22 wherein the organometallic compound of a metal other than zinc comprising a non-aromatic moiety is an optionally substituted $C_{1-6}$alkyl magnesium halide, an optionally substituted $C_{1-6}$alkyl lithium or an optionally substituted $C_{1-6}$alkyl lithium halide.

29. A process according to claims 21 or 22 wherein the organometallic compound of a metal other than zinc comprising an aromatic moiety is phenyl lithium and the organometallic compound of a metal other than zinc comprising a non-aromatic moiety is selected from the group consisting of methyllithium, trifluoromethyllithium, ethyllithium, n-propyllithium, iso-propyllithium, n-butyllithium, iso-butyllithium, and tert-butyllithium.

* * * * *